United States Patent [19]

Lappi et al.

[11] 4,018,780
[45] Apr. 19, 1977

[54] [1]BENZOTHIENO[3,2-F]QUINOLINECARBOXYLIC ACIDS

[75] Inventors: Larry R. Lappi, Stillwater; Edward H. Erickson, Woodbury, both of Minn.

[73] Assignee: Riker Laboratories, Inc., Northridge, Calif.

[22] Filed: Aug. 25, 1975

[21] Appl. No.: 607,626

[52] U.S. Cl. .................. 260/287 C; 260/330.5; 260/332; 260/485 N; 260/578; 424/258

[51] Int. Cl.² .................................... C07D 495/22

[58] Field of Search ............... 260/287 C, 283 S; 424/258

Primary Examiner—Donald G. Daus
Assistant Examiner—David E. Wheeler
Attorney, Agent, or Firm—Cruzan Alexander; Donald M. Sell; Carolyn A. Bates

[57] ABSTRACT

4-Hydroxy[1]benzothieno[3,2-f]quinoline-2-carboxylic acids and esters thereof are prepared by the reaction of an optionally substituted 2-aminobenzothiophene with dimethyl acetylenedicarboxylate followed by ring closure. The sulfur atom of the intermediate compounds in the process can be oxidized to oxide or dioxide state, then hydrolyzed to the acids, or first hydrolyzed to the acids and then oxidized, if desired. The acids are physiologically active as anti-allergic agents in the acid form or as salts.

21 Claims, No Drawings

[1]BENZOTHIENO[3,2-F]QUINOLINECARBOXYLIC ACIDS

BACKGROUND OF THE INVENTION

This invention relates to novel anti-allergic agents which are optionally substituted 4-hydroxy[1]benzothieno[3,2-f]-quinoline-2-carboxylic acids and salts thereof, to novel intermediates useful for the synthesis of said anti-allergic agents, to processes for the synthesis of said anti-allergic agents and to methods for the use of these novel anti-allergic agents.

The basic ring structure of the compounds of the present invention is novel. The closest known ring structures having the ring sequence $C_4S,C_5N,C_6,C_6$ are believed to be [1]-benzothieno[2,3-b]quinoline, [1]benzothieno[3,2-b]quinoline, thieno[3,2-c]acridine, thieno[3,4-c]acridine and thieno[2,3-c]-acridine as reported in "The Ring Index", Reinhold Publishing Company, 1940.

DETAILED DESCRIPTION OF THE INVENTION

This invention relates to physiologically active compounds of the formula (I)

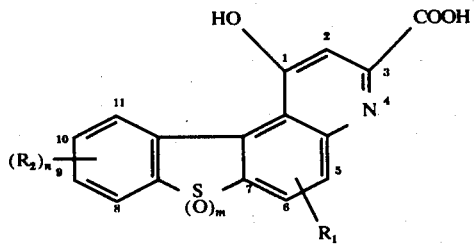

wherein $R_1$ is hydrogen, halogen, lower alkyl or lower alkoxy, $R_2$ is halogen, lower alkyl and/or lower alkoxy, $m$ is zero, one or two and $n$ is zero, one or two, and lower alkyl esters and pharmaceutically acceptable salts thereof. This invention is also related to novel intermediates useful for the synthesis of compounds of formula (I), to processes for the synthesis of compounds of the present invention and to methods for the use of compounds of formula (I) as anti-allergic agents.

Compounds of formula (I) wherein $n$ is zero or one, $m$ is one or two, and $R_2$ substituents are in the 8, 9 or 10 positions are preferred from the standpoint of their physiological activity, i.e. higher potency. Particularly preferred compounds of formula (I) are those in which the benzothiophene moiety is unsubstituted, i.e. $n$=zero. Most preferred substituted compounds are those wherein $R_2$ substituents are in the 8 or 10 positions, particularly wherein $R_2$ is halogen, methyl or methoxy in the 8 position.

Compounds of the invention wherein $R_1$ is methoxy or halogen form a presently preferred subclass.

The term "lower" when used herein to apply to alkyl or alkoxy means containing one to six carbon atoms in straight or branched chains.

Compounds of the invention particularly useful as presently known are:
1-hydroxy[1]benzothieno[3,2-f]quinoline-3-carboxylic acid-7,7-dioxide;
1-hydroxy-10-methyl[1]benzothieno[3,2-f]quinoline-3-carboxylic acid-7-oxide;
1-hydroxy-10-methyl[1]benzothieno[3,2-f]quinoline-3-carboxylic acid-7,7-dioxide;
1-hydroxy-10-methoxy[1]benzothieno[3,2-f]quinoline-3-carboxylic acid-7,7-dioxide;
6-chloro-1-hydroxy[1]benzothieno[3,2-f]quinoline-3-carboxylic acid-7,7-dioxide;
8-chloro-1-hydroxy[1]benzothieno[3,2-f]quinoline-3-carboxylic acid-7,7-dioxide;
1-hydroxy-6-methoxy[1]benzothieno[3,2-f]quinoline-3-carboxylic acid-7,7-dioxide;
1-hydroxy-8-methyl[1]benzothieno[3,2-f]quinoline-3-carboxylic acid-7,7-dioxide;
1-hydroxy-5-methoxy[1]benzothieno[3,2-f]quinoline-3-carboxylic acid-7,7-dioxide;
5-bromo-1-hydroxy[1]benzothieno[3,2-f]quinoline-3-carboxylic acid-7,7-dioxide;
9-chloro-1-hydroxy[1]benzothieno[3,2-f]quinoline-3-carboxylic acid-7,7-dioxide; and
5-bromo-1-hydroxy[1]benzothieno[3,2-f]quinoline-3-carboxylic acid-7-oxide.

The general outline of the process for preparation of compounds of the invention is illustrated by the following reaction sequence.

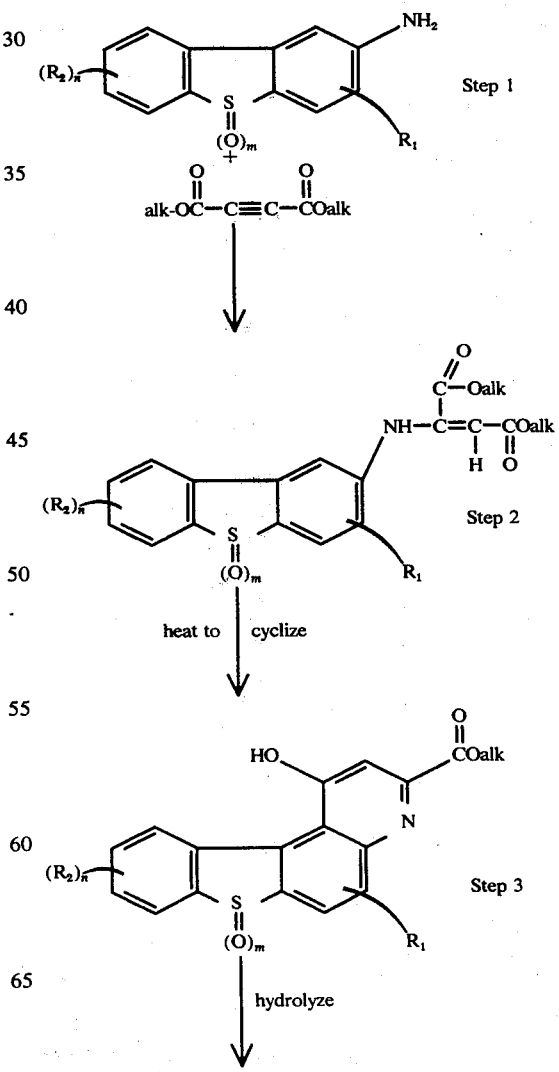

-continued

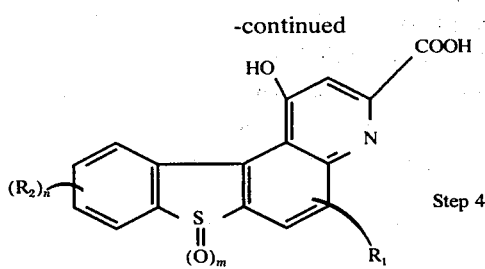

Step 4

Compounds of the invention are prepared starting with an optionally substituted 2-aminodibenzothiophene and reacting with dimethyl acetylenedicarboxylate or other di(lower alkyl) acetylenedicarboxylate esters. The novel intermediates formed are N-2-(dibenzothienyl)aminofumarates. The reaction is generally carried out in a suitable non-reactive solvent such as a lower alkanol, for example, methanol or ethanol, a lower alkyl ether, for example, dimethyl ether, tetrahydrofuran, a lower alkyl ester of an organic acid, for example, ethyl acetate and the like.

The reaction occurs readily at moderate temperatures such as 0° to 100° C. It is presently preferred to use ambient temperatures such as about 23° C. The reaction proceeds rapidly, but the product is quite stable under the preferred reaction conditions, and reaction time may be extended, if desired, until analysis, for example thin layer chromatographic analysis, shows that no further reaction is occuring. Generally a slight to moderate excess of a dialkyl acetylenedicarboxylate is used, but equimolar quantities of the reactants are used with acceptable results. The fumarate products are readily isolated by conventional techniques.

The novel di(lower alkyl) N-(dibenzothienyl)-aminofumarates thus formed are condensed by heating in a suitable inert solvent to provide novel lower alkyl 1-hydroxy[1]-benzothieno[3,2-f]quinoline-3-carboxylates. Suitable solvents for this reaction are diaryl ethers; for example, diphenyl ether, mixtures of diphenyl ether and biphenyl, mineral oil and other inert high boiling solvents. Reaction time to completion will, of course, vary with the solvent and the temperature used but is generally one to thirty minutes and temperatures of 200° to 300° C. can thus be employed.

Alternatively, this condensation reaction is accomplished by heating the fumarate intermediate in polyphosphoric acid. A temperature in the range of 100 to 180° C. can be used. The reaction time is temperature-dependent but is generally less than one day and preferably one hour or less.

The hydrolysis of the lower alkyl 1-hydroxy[1]-benzothieno[3,2-f]quinoline-3-carboxylates to the desired final product acids is carried out under either acidic or basic conditions. Acidic hydrolysis using inorganic acids such as hydrochloric acid, sulfuric acid and the like is carried out by heating in a suitable solvent, particularly a very polar solvent such as N,N-dimethylformamide. Basic hydrolysis is accomplished by heating at from 25° to 110° C. in aqueous media with an inorganic base such as sodium hydroxide, potassium hydroxide and the like, optionally in a suitable solvent such as a lower alkanol, for example ethanol, or N,N-dimethylformamide, tetrahydrofuran and other inert solvents.

Compounds of the invention wherein $m$ is one or two may be prepared by oxidizing a lower alkyl 1-hydroxy[1]benzothieno[3,2-f]quinoline-3-carboxylate as produced in Step 2, which may be oxidized, for example with hydrogen peroxide in acetic acid, to provide an ester of a compound of formula (I) wherein $m$ is one or two. This ester is then hydrolyzed as described hereinabove to the desired acid of formula (I).

Alternatively the final product acid of formula (I) wherein $m$ is zero may be oxidized directly to a compound of formula (I) wherein $m$ is one or two, or a compound wherein $m$ is one may be oxidized to a compound wherein $m$ is two.

Again, an acid of formula (I) wherein $m$ is one or two may be prepared by starting with a 3-substituted 2-aminodibenzothiophene 5-oxide or 5,5-dioxide and reacting with dimethyl acetylenedicarboxylate as described above, to obtain a 5-oxidized di(lower alkyl) N-2-dibenzothienylaminofumarate which is condensed as described above to provide a 5-oxidized lower alkyl 1-hydroxy[1]benzothieno[3,2-f]quinoline-3-carboxylate, which is hydrolyzed as described above to the desired final product acid.

Functional derivatives of the compounds according to the invention include salts, notably water-soluble salts, and esters of the carboxylic acid function which is present.

Salts of the compounds which are preferred are salts with physiologically acceptable cations, for example ammonium salts; metal salts, such as alkali metal salts (e.g. sodium, potassium and lithium salts) and alkaline earth metal salts (e.g. magnesium and calcium salts); and salts with organic bases, e.g. amine salts derived from mono-, di- or tri-lower alkyl or lower alkanolamines (such as triethanolamine or triethylamine) and salts with heterocyclic amines such as piperidine, pyridine and morpholine.

Compounds having an ester group are also useful for the purposes of the invention. Some of these esters are also physiologically active like the acids, while the others are useful intermediates and readily converted to the acids by hydrolysis.

The new compounds of the invention of formula (I) have been shown to inhibit the release and/or synthesis and/or effect of biochemical products brought on in the mammalian organism by the combination of certain types of antibody and specific antigen. In man, both subjective and objective changes which result from the inhalation of specific antigen by sensitized subjects may be markedly inhibited by administration of the new compounds. The new compounds are useful in the treatment of so-called "intrinsic" asthma (in which no sensitivity to extrinsic antigen can be demonstrated) or any condition in which non-specific factors trigger the release of allergic mediators and in the treatment of other conditions in which antigen-antibody reactions are responsible for disease, for example extrinsic asthma, food allergies, allergic rhinitis, allergic conjunctivitis, atopic dermatitis, hay fever, urticaria and auto-immune diseases.

A further embodiment of the invention, therefore, is a pharmaceutical composition comprising a compound of formula (I), or a derivative thereof, preferably in the form of a salt, in association with a pharmaceutically acceptable carrier or diluent.

The nature of the composition and the pharmaceutically acceptable carrier or diluent will, of course, depend upon the desired mode of administration, which may be, for example, orally; by inhalation; parenterally; or by topical application.

The pharmaceutical compositions of the invention may be formulated in the conventional manner with the customary ingredients. For example, the compositions may be put up as aqueous solutions or suspensions, as dry powders, or in tablet, cream, lotion or syrup form.

The compositions of the invention generally comprise a minor proportion of the compound of formula (I) and a major proportion of carrier or diluent. Thus, for example, aqueous solutions for administration by means of a conventional nebulizer may contain up to about 10 percent by weight of the active ingredient in sterile water; and compositions for dispensing from a pressurized container comprising suspensions or solutions in liquified propellants will contain, for example, about 0.2 to 5 percent by weight of the active ingredient.

The compounds of formula (I) are preferably administered by inhalation, notably in the treatment of allergic asthma. For such use, the compounds of formula (I), preferably in the form of a salt such as the sodium salt, are dissolved or suspended in water and may be applied by means of a conventional mebulizer. However, the administration of medicaments by means of a pressurized dispensing container, i.e. an aerosol dispenser, is an alternative to nebulizer administration.

For administration from an aerosol dispenser, the medicament is dissolved or suspended in a liquefied propellant medium. The propellants for present use may be any of those which are conventionally used in formulations for dispensing from pressurized containers. For example, they may be of the halogenated hydrocarbon-type such as fluoro- or fluorohalo- hydrocarbons and mixtures of any of these together with other propellents.

Typical suitable propellants are disclosed in, for example, U.S. Pat. No. 2,868,691. Preferred propellants of low toxicity are difluorodichloromethane, dichlorotetrafluoroethane or mixtures thereof. Where the medicament is not soluble in the propellant, it may be necessary to add a surface-active agent to the composition in order to suspend the medicament in the propellant medium, and such surface-active agents may be any of those commonly used for this purpose, such as non-ionic surface active agents. The use of such surface-active agents and the advantages which stem therefrom are more fully described in British Patent Specification No. 1,063,512.

The compositions of the invention may also be administered in the form of powder by means of an insufflator device of the conventional type. In order to improve the properties of the powder for this purpose it is useful to modify the surface characteristics of the powder particles, for example, by coating them with a pharmaceutically acceptable material such as sodium stearate. In addition, finely divided powders of the active ingredients may be mixed with a coarser diluent material, such as lactose, which may be present in a smaller, equal or greater amount that the active ingredients, for example in from 50 to 150 percent by weight based on the weight of the compound of formula (I) and such other active ingredients as may be present.

The compounds of the invention may also be administered by dispensers from which metered amounts of the compound are discharged in a state to be orally received during inhalation, wherein the propellant is compressed air or other compressed inert gas such as nitrogen, argon and the like.

Whilst the inhalation of medicament has been described above with particular reference to oral administration, it will be appreciated that it may be desirable to administer the medicament nasally. The term inhalation is therefore used herein to denote, where the context permits, both oral and nasal administration.

The compositions of the invention are also effective in treating certain allergic reactions when administered orally in tablets, syrups and the like or by intradermal or intravenous injection in the conventional manner.

The compounds for formula (I) may also find use in the treatment of allergic eye conditions, for example that associated with hay fever, i.e. allergic conjunctivitis. For such use the compound of formula (I) may be used in the form of an eye drop and/or spray as an isotonic aqueous solution containing about two percent of the compound and a preservative.

In addition to the internal administration, the compounds of formula (I) find use in compositions for topical application, e.g. as creams, lotions or pastes for use in dermatological treatments.

In addition to the compounds of formula (I) and the ingredients required to present the compound in a form suitable for the selected mode of administration, other active ingredients may be present in the composition of the invention. Thus, in compositions for administration by inhalation, it may be beneficial to include a bronchodilator. Suitable bronchodilators include those known to the art such as isoprenaline, adrenaline, carbuterol, rimiterol, orciprenaline, isoetharine and derivatives thereof, particularly the salts thereof. The amount of bronchodilator used will vary over a broad range, depending, inter alia, upon the nature and activity of the bronchodilator and the compound of formula (I) used. However, the use of a minor proportion (i.e. less than 50 percent by weight) of the bronchodilator is preferred. The use of from 0.1 to 10 percent by weight of the bronchodilator based on the weight of the compound of formula (I) is particularly preferred. Another embodiment of the invention thus is a composition which comprises a compound of formula (I) or a derivative thereof in admixture with a bronchodilator, which latter is preferably present in less than 50 percent, especially 0.1 to 10 percent by weight of the former.

As described hereinabove, the compounds of formula (I) are indicated for use in inhibiting the effects of antibody-antigen reactions. In such treatment, the compound or composition of the invention is administered by the chosen method to the site of the antibody-antigen reaction in the therapeutically effective amount. The treatment may be one which requires repeated dosages of the medicament at regular intervals. The amount of medicament and frequency of administration will depend upon many factors, and no concise dosage rate or regimen can be generally stated. However, as a general guide, where the compounds are administered by inhalation to a patient suffering from acute allergic asthma, therapeutically useful results may be achieved when doses of 0.1 to 20 mg/kg are used. When the compounds are administered by oral routes, larger dosages are given.

The invention thus also provides a method for inhibiting the effects of an antibody-antigen reaction which comprises the prior (preferably) or subsequent application to the known or expected area of the antibody-antigen reaction mechanism of a therapeutically effective amount of a compound of formula (I) or a derivative thereof.

The effectiveness of the compounds of the invention in inhibiting passive cutaneous anaphylaxis in a standard test method substantially as described in "Immunology", 16, 749 (1969).

The variation of the method generally used was as follows: Sprague-Dawley rats (male or female) having a body weight of about 200 grams were injected intramuscularly with egg albumin and intraperitoneally with *Bordetella pertussis* vaccine. Ten to twelve days after this treatment the rats were exanguinated via the abdominal aorta to recover the blood, which was allowed to clot overnight. The blood samples were centrifuged in order to remove the blood serum containing the antibody.

This antibody was used in the following way: Sprague-Dawley rats in the body weight range of 50 to 120 grams were sensitized by intradermal injection of 0.1 ml. an antibodycontaining serum into the mid-dorsal region. Sensitivity was allowed to develop for 24 hours, and the rats were then injected intravenously with the antigen which comprises 1 ml. of a mixture of egg albumin (0.5 mg/ml), Evans Blue dye solution (10 mg/ml) and physiological saline. Test compounds were administered either as intraperitoneal injection or orally at various times (e.g. five minutes) and at various dose levels before intravenous administration of egg albumin and Evans Blue dye. For each concentration of the compound under test, six rats were injected. Six rats were used as controls in each test. The dose levels of the compound under test were selected so as to give a range of inhibition values. Suitable screening doses are 50, 25, 10 or 5 mg/kg.

Forty-five minutes after injection of egg albumin the rats were killed and the skins removed and reversed. The intensity of the anaphylactic reaction was assessed by comparing the size (i.e. area determined from products from two diameters taken at right angles) of the characteristic blue weal produced by spread of the Evans Blue dye from the sensitization site. Calculations are done by comparing with the size of the weal in the control animals to yield a percent inhibition.

$$\frac{(\text{Control group area - treated group area}) \times 100}{\text{Control group area}}$$

If the percentage inhibitions for the various dose levels are plotted graphically for each compound, the dosage required to achieve a 50 percent inhibition of the anaphylactic reaction ($ID_{50}$) may be determined from these graphs.

It has been proven that this test method gives reliable qualitative indications of the ability of the compounds under test to inhibit antibody-antigen reactions in man.

Many of the compounds of the invention are phosphodiesterase inhibitors and some of them of them have been shown to increase cyclic-AMP levels in mammals.

The compounds of the invention have been found to be effective when administered in aerosol form to dogs and monkeys to protect these animals against an aerosol of an *Ascaris* extract to which they normally would exhibit an asthmalike response.

The invention may be further illustrated by the following illustrative examples, which should not be construed to limit the invention.

EXAMPLE 1

A mixture of 29.7 g. (0.231 mole) of 4-fluorothiophenol, 41 g. (0.238 mole) of 2-chloro-5-nitroaniline and 14.9 g. (0.266 mole) of potassium hydroxide in 500 ml. of 95 percent aqueous ethanol is heated to its reflux temperature and maintained at reflux for one hour, then cooled with an ice bath. Some crude product is isolated as a solid by filtration, then the filtrate is diluted with water and extracted with four 300 ml. portions of chloroform. The combined extracts are washed with four 300 ml. portions of water and then with saturated sodium chloride solution and dried. Evaporation under vacuum provides a residue which is combined with the previously isolated crude solid product, 2-(4-fluorophenylthio)-5-nitroaniline. The solid is dissolved in 500 ml. of chloroform, then the solution is saturated with hydrogen chloride gas. The white precipitate which forms is separated by filtration, washed with chloroform and diethyl ether and dried to provide 2-(4-fluorophenylthio)-5-nitroaniline hydrochloride.

EXAMPLE 2

To a stirred suspension of 55 g. (0.183 mole) of 2-(4-fluorophenylthio)-5-nitroaniline hydrochloride in 450 ml. of acetic acid at 16 to 18° C. is added dropwise 18.6 g. (0.181 mole of n-butyl nitrite during a period of 20 minutes. The solution is then diluted with 1.5 liters of cold (12° C.) of 50 percent aqueous acetic acid. The solution is maintained at 10 to 12° C., and 68 g. of copper powder are added in small portions during a period of 15 minutes. After stirring at 10° to 15° C. for an additional 20 minutes, the mixture is heated and stirred at 50° C. for 1 hour. The mixture is cooled to 5° C. and filtered. The solid residue is washed thrice with 300 ml. of aqueous sodium hydroxide, then thrice with 300 ml. of distilled water. The brown solid is dissolved in hot benzene, filtered and the hot filtrate treated with decolorizing charcoal. The benzene is evaporated to give a residue which is twice recrystallized from benzene to give off-white crystals of 2-fluoro-8-nitrodibenzothiophene, m.p. 200°–202° C.

EXAMPLES 3

A mixture of 14.33 g. (0.0605 mole) of 2-fluoro-8-nitrodibenzothiophene in 550 ml. of ethanol and about one-half teaspoonful (about 2.5 ml.) of Raney nickel is hydrogenated at about 30 psi of hydrogen gas in a Paar apparatus for about 48 hours. The mixture is filtered, and the filtrate is evaporated to dryness under vacuum to provide white needles of 2-amino-8-fluorodibenzothiophene, m.p. 131°–132° C.

EXAMPLE 4

Using the method of Examples 1 to 3 and starting with the appropriately substituted thiophenols and chloro- or bromo-nitroanilines the following substituted aminodibenzothiophenes are prepared and may be used after filtration to remove the catalyst without further purification.

2-amino-7-chlorodibenzothiophene, m.p. 112°–115° C.
2-amino-8-bromodibenzothiophene, m.p. 142°–144°C.
2-amino-8-chlorodibenzothiophene, m.p. 125°–135° C.
2-amino-8-methyldibenzothiophene
2-amino-8-methoxydibenzothiophene, m.p. 230°–240° C.

2-amino-8n-hexyloxydibenzothiophene, m.p. 40°–60° C.
2-amino-6-chlorodibenzothiophene, m.p. 140°–150° C.
2-amino-6-methoxydibenzothiophene, m.p. 180°–185° C.
2-amino-4-chlorodibenzothiophene, m.p. 86°–90° C.
2-amino-4-methoxydibenzothiophene
2-aminodibenzothiophene, m.p. 128°–129° C.
2-amino-3-bromodibenzothiophene-5,5-dioxide, m.p. 290°–295° C.
2-amino-6-methyldibenzothiophene, m.p. 120°–123° C.
2-amino-3-methoxydibenzothiophene
2-amino-7-methyldibenzothiophene, m.p. 85°–90° C.
2-amino-7-methyl-8-bromodibenzothiophene, m.p. 191°–195° C.
2-amino-9-chlorodibenzothiophene, m.p. 120°–125° C.
2-amino-8-isopropyldibenzothiophene
2-amino-8-n-hexyldibenzothiophene
2-amino-6-fluorodibenzothiophene
2-amino-6-isopropoxydibenzothiophene
2-amino-4-fluorodibezothiophene
2-amino-4-n-butyldibenzothiophene
2-amino-4-methyldibenzothiophene
2-amino-4-n-butoxydibenzothiophene
2-amino-8-n-butyldibenzothiophene

EXAMPLE 5

To a stirred mixture of 12.5 g. (57.6 mmoles) of 2-amino-8-fluorodibenzothiophene in 200 ml. of methanol are added dropwise 10 g. (70.5 mmoles) of dimethyl acetylenedicarboxylate. The mixture is stirred at about 23° C. for about 16 hours. The mixture is cooled in an ice bath, and the resulting yellow solid is isolated by filtration. The yellow crystalline product, dimethyl N-2-(8-fluorodibenzothienyl) aminofumarate, is recrystallized from an ethanol-hexane mixture to provide product with m.p. 129°–132° C.

Using the method of Example 5 and using starting materials prepared, for example, as described in Examples 1 to 4, the following novel intermediates are prepared.

TABLE I

| Ex. No. | Starting Material | Fumarate Product | Melting Point (in °C.) |
|---|---|---|---|
| 6 | (structure with NH, Cl) | (structure with NHC=CHCO₂CH₃, CO₂CH₃, Cl) | 158–164 |
| 7 | (structure with Br, NH₂) | (structure with Br, NHC=CHCO₂CH₃, CO₂CH₃) | 150–166 |
| 8 | (structure with NH₂) | (structure with NHC=CHCO₂CH₃, CO₂CH₃) | 132.5–134 |
| 9 | (structure with CH₃, NH₂) | (structure with CH₃, NHC=CHCO₂CH₃, CO₂CH₃) | — |
| 10 | (structure with CH₃O, NH₂) | (structure with CH₃O, NHC=CHCO₂CH₃, CO₂CH₃) | 120–128 |
| 11 | (structure with Cl, NH₂) | (structure with Cl, NHC=CHCO₂CH₃, CO₂CH₃) | 158–163 |
| 12 | (structure with NH₂, Cl) | (structure with NHC=CHCO₂CH₃, CO₂CH₃, Cl) | 103 |
| 13 | (structure with NH₂, OCH₃) | (structure with NHC=CHCO₂CH₃, CO₂CH₃, CH₃O) | 159–161 |
| 14 | (structure with NH₂, Cl) | (structure with NHC=CHCO₂CH₂CH₃, CO₂CH₂CH₃, Cl) | 128–132 |

TABLE I-continued

| Ex. No. | Starting Material | Fumarate Product | Melting Point (in °C.) |
|---|---|---|---|
| 15 | [benzothiophene-S,S-dioxide with NH₂ and Br substituents] | [corresponding fumarate: NHC=CHCO₂CH₃, CO₂CH₃] | — |
| 16 | H(CH₂)₆O-[benzothiophene]-NH₂ | H(CH₂)₆O-[benzothiophene]-NHC=CHCO₂CH₃, CO₂CH₃ | — |
| 17 | [benzothiophene with NH₂ and OCH₃ substituents] | [corresponding fumarate] | — |
| 18 | [benzothiophene with NH₂ and CH₃ substituents] | [corresponding fumarate] | 126–128 |
| 19 | [benzothiophene with NH₂ and OCH₃ substituents] | [corresponding fumarate] | 103–105 |
| 20 | CH₃-[benzothiophene]-NH₂ | CH₃-[benzothiophene]-NHC=CHCO₂CH₃, CO₂CH₃ | 129–133 |
| 21 | Br-[benzothiophene with CH₃]-NH₂ | Br-[benzothiophene with CH₃]-NHC=CHCO₂CH₃, CO₂CH₃ | 162–170 |
| 22 | [benzothiophene with NH₂ and F substituents] | [corresponding fumarate] | — |
| 23 | Cl-[benzothiophene]-NH₂ | Cl-[benzothiophene]-NHC=CHCO₂CH₃, CO₂CH₃ | 145–148 |
| 24 | (CH₃)₂CH-[benzothiophene]-NH₂ | (CH₃)₂CH-[benzothiophene]-NHC=CHCO₂CH₃, CO₂CH₃ | — |
| 25 | H(CH₂)₃O-[benzothiophene]-NH₂ | H(CH₂)₃O-[benzothiophene]-NHC=CHCO₂CH₃, CO₂CH₃ | — |
| 26 | [benzothiophene with NH₂ and F substituents] | [corresponding fumarate] | — |
| 27 | [benzothiophene with NH₂ and (CH₃)₂CHO substituents] | [corresponding fumarate] | — |

TABLE I-continued

| Ex. No. | Starting Material | Fumarate Product | Melting Point (in °C.) |
|---|---|---|---|
| 28 | 1-methoxy-dibenzothienyl-amine (CH₃O substituted) | dimethyl N-(1-methoxydibenzothienyl)aminofumarate | — |
| 29 | methyl-dibenzothienyl-amine (CH₃ substituted) | dimethyl N-(methyldibenzothienyl)aminofumarate | — |
| 30 | butyl-dibenzothienyl-amine (H(CH₂)₄ substituted) | dimethyl N-(butyldibenzothienyl)aminofumarate | — |

EXAMPLE 31

A solution of 15.85 g. (0.0441 mole) of dimethyl N-2-(8-fluorodibenzothienyl)aminofumarate in 125 ml. of diphenyl ether is heated to 240° C. and maintained at that temperature for about five minutes, then allowed to cool to about 23° C. The solution is mixed with 400 ml. of hexane and cooled with an ice bath. The solid product is filtered to provide a yellow solid which is recrystallized from a mixture of N,N-dimethyl formamide and water to provide methyl 1-hydroxy-10-fluoro[1]benzothieno[3,2-f]quinoline-3carboxylate, m.p. 269°-271° C. Analysis: Calculated for $C_{17}H_{10}FNO_3S$: %C, 62.4; %H, 3.1; %N, 4.3; Found: %C, 62.7; %H, 3,3; %N, 4.4.

EXAMPLE 32

A mixture of 2.0 g. (0.0065 mole) of methyl 1-hydroxy[1]benzothieno[3,2-f]quinoline-3-carboxylate (about 90 percent pure) in N,N-dimethyl formamide is heated to its reflux temperature, and several drops of 10 percent aqueous hydrochloric acid are added every fifteen minutes for 2 hours. The resulting yellow solid is separated by filtration to provide 1-hydroxy[1]benzothieno[3,2-f]quinoline-3-carboxylic acid, m.p. >285° C. (dec.). Analysis: Calculated for $C_{16}H_9NO_3S$: %C, 65.1; %H, 3.1; %N, 4.7; Found: %C, 64.9; %H, 2.9; %N, 4.8. Purity is greater than 98 percent according to nuclear magnetic resonance spectral analysis.

EXAMPLES 33

A mixture of 1.5 g. (0.005 mole) of methyl 1-hydroxy[1]benzothieno[3,2-f]quinoline-3-carboxylate and 40 ml. of 10 percent aqueous sodium hydroxide in 40 ml. of ethanol is heated to its reflux temperature and maintained at reflux for two hours. The mixture is filtered, then evaporated under vacuum to provide a residue which is washed with benzene. The solid residue is added to 50 ml. of stirred 10 percent hydrochloric acid. The mixture is stirred for twenty minutes, then filtered to provide a solid residue which is washed several times with water. The yellow product is 1-hydroxy[1]benzothieno[3,2-f]quinoline-3-carboxylic acid hydrate, m.p. 290° C. (dec.). Analysis: Calculated for $C_{16}H_9NO_3S \cdot 1/4H_2O$: %C, 64.1; %H, 3.2; %N, 4.7; Found: %C, 63.9; %H, 3.3; %N, 4.6.

EXAMPLE 34

To a solution of 4 g. (0.013 mole) of methyl 1-hydroxy[1]benzothieno[3,2-f]quinoline-3-carboxylate in glacial acetic acid is added a 10-fold excess of 30 percent hydrogen peroxide. The mixture is heated to its reflux temperature and maintained at reflux for about 1 hour, then allowed to cool. The resulting precipitate is separated by filtration. The yellow solid product is methyl 1-hydroxy[1]benzothieno[3,2-f]-quinoline-3-carboxylate-7,7-dioxide, m.p. 295° C. (dec.). Analysis: Calculated for $C_{17}H_{11}NO_5S$: %C, 59.8; %H, 3.25; %N, 4.1; Found: %C, 59.5; %H, 3.0; %N, 4.1.

EXAMPLE 35

When the product of Example 34 is hydrolyzed using the method of Example 32 or Example 33 the product is 1-hydroxy[1]benzothieno[3,2-f]quinoline-3-carboxylate-7,7-dioxide hydrate, m.p. 290°C. (dec.). Analysis: Calculated for $C_{16}H_9NO_5S \cdot 3/4H_2O$: %C, 56.4; %H, 3.1; %N, 4.1; Found: %C, 56.6; %H, 3.3; %N, 4.1.

The free acid (0.1 mole) of 1-hydroxy[1]benzothieno[3,2-f]quinoline-3-carboxylate-7,7-dioxide is reacted with 0.1 mole of sodium bicarbonate in 300 ml. of water, evaporated and the residue recrystallized from an ethanol-water mixture to give the sodium salt as a yellow powder, m.p. >300° C. Analysis: Calculated for $C_{16}H_8NNaO_5S \cdot 1/2H_2O$: %C, 53.6; %H, 2.5; %N, 3.91; Found: %C, 53.6; %H, 2.5; %N, 4.1.

Using the method of Example 31 and starting with dialkyl N-2-(dibenzothienyl) aminofumarates prepared, for example, as described in Example 5, esters of the invention listed in Table II are prepared. The esters of Table II are converted to the corresponding acids of Table II using, for example, the methods described in Examples 32 to 35.

TABLE II

| Ex. No. | Structure | Melting Point (in °C) Esters Q=CH₃ | Acids Q=H |
|---|---|---|---|
| 36 | (HO, COOQ; Cl-benzothiophene fused) |  | 350 (dec) |
| 37 | (HO, COOQ; Cl-benzothiophene-SO₂ fused) | 313–314 (dec) | 293–295 (dec) |
| 38 | (HO, COOQ; Br-benzothiophene-SO₂ fused) | 293 (dec) | 316 (dec) |
| 39 | (HO, COOQ; Br-benzothiophene-S fused) | 324–326 (dec) | 310–311 (dec) |
| 40 | (HO, COOQ; CH₃-benzothiophene-S fused) | 268 (dec) | 310–312 (dec) |
| 41 | (HO, COOQ; CH₃-benzothiophene-SO₂ fused) | 331–333 (dec) | 302–304 (dec) |
| 42 | (HO, COOQ; OCH₃-benzothiophene-S fused) | 260–263 (dec) | 305–307 (dec) |
| 43 | (HO, COOQ; OCH₃-benzothiophene-SO₂ fused) |  | 296–298 (dec) |
| 44 | (HO, COOQ; F-benzothiophene-S fused) | 269–271 (dec) | 308 (dec) |

TABLE II-continued
| Ex. No. | Structure | Melting Point (in °C) Esters Q=CH₃ | Acids Q=H |
|---|---|---|---|
| 45 | 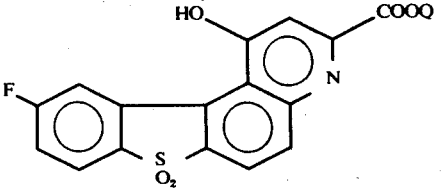 | 305–307 (dec) | 389–291 (dec) |
| 46 | 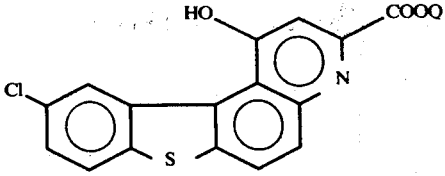 | 288–289 (dec) | 308–309 (dec) |
| 47 | 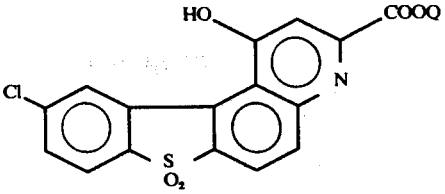 | | 307–308 (dec) |
| 48 | 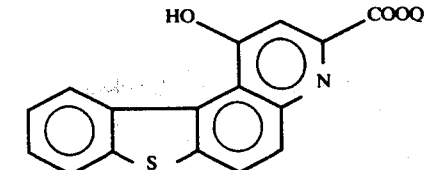 | | 300–302 (dec) |
| 49 | 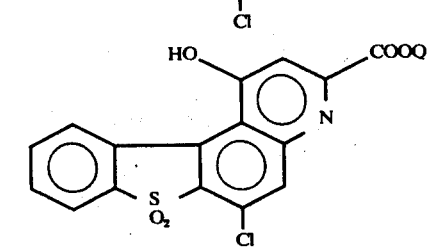 | | 308–309 (dec) |
| 50 | 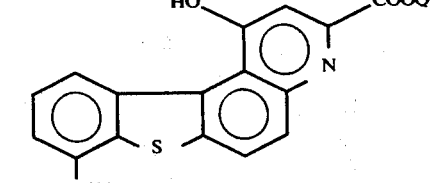 | 260–262 (dec) | 305–306 (dec) |
| 51 | 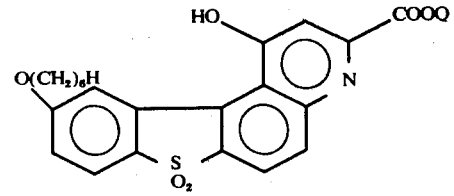 | | 288–289 (dec) |
| 52 | 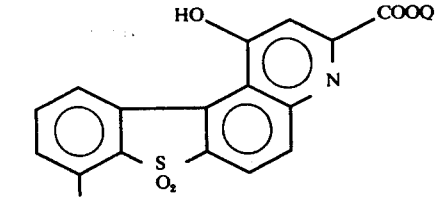 | 315–316 (dec) | 285–287 (dec) |

TABLE II-continued

| Ex. No. | Structure | Melting Point (in °C) Esters Q=CH₃ | Acids Q=H |
|---|---|---|---|
| 53 | (structure) | | 301–302 (dec) |
| 54 | (structure) | 272–275 (dec) | 297–298 (dec) |
| 55 | (structure) | | 299–300 (dec) |
| 56 | (structure) | 322–323 | 309–310 (dec) |
| 57 | (structure) | | 293–295 (dec) |
| 58 | (structure) | | 348–350 (dec) |
| 59 | (structure) | | 302–304 (dec) |
| 60 | (structure) | | 315 (dec) |

TABLE II-continued

| Ex. No. | | Melting Point (in °C) Esters Q=CH₃ | Acids Q=H |
|---|---|---|---|
| 61 | (structure: HO, COOQ, Cl, S, N — chlorodibenzothiophene-hydroxyquinoline carboxylate) | | 319 (dec) |

EXAMPLE 62

Part A — 2-Bromodibenzothiophene

To a stirred, cold solution (0° C.) of 275 g. of dibenzothiophene in 1 liter of chloroform is added over 30 minutes 253 g. of bromine in 500 ml. of chloroform. After sixteen hours of stirring the mixture is heated to its reflux temperature and maintained at reflux for about 30 minutes. The mixture is then evaporated, and 900 ml. of ethanol are added to the residue. The white solid collected by filtration is 2-bromodibenzothiophene, m.p. 112°–116° C.

Part B — 2-Bromodibenzothiophene-5-oxide

Into a cold suspension of 200 g. of 2-bromodibenzothiophene in about 500 ml. of carbon tetrachloride is bubbled over 30 minutes about 60 g. of chlorine gas. The mixture is poured into 1.5 liters of ice and water and stirred overnight. The solid product is separated by filtration and dissolved in benzene. The mixture is distilled to remove the benzene-water azeotrope, filtered hot and the filtrate is cooled. The product, 2-bromodibenzothiophene-5-oxide, is separated by filtration and further product is obtained by partial evaporation of the solvent.

Part C — 2-Aminodibenzothiophene-5-oxide

A mixture of 150 g. of crude 2-bromodibenzothiophene-5-oxide, 160 g. of cuprous bromide and 1700 ml. of ammonium hydroxide is heated at 200° C. in a pressure reactor for about 12 hours. The mixture is then filtered, and the residue is washed with water, then heated in methanol and filtered hot. The product is recrystallized by cooling and separated by filtration to give 2-aminodibenzothiophene-5-oxide, m.p. 169°–172° C.

EXAMPLE 63

To a solution of 20 g. of 2-aminodibenzothiophene-5-oxide in 75 ml. of acetic acid are added dropwise with stirring 14 g. of bromine. After stirring overnight, 250 ml. of water are added, and the resulting precipitate is separated by filtration. The product is assigned the structure 2-amino-3-bromodibenzothiophene-5-oxide with the assistance of nuclear magnetic resonance spectral analysis.

A mixture of 1.0 g. of dimethyl acetylenedicarboxylate and 0.90 g. of 2-amino-3-bromodibenzothiophene-5-oxide in methanol solution is heated to its reflux temperature and maintained at reflux for 30 minutes. The reaction mixture is then heated on a steam bath to evaporate to dryness. The residue is taken up in methanol and separated by filtration to provide dimethyl N-2-(3-bromodibenzothienyl)fumarate-5-oxide, m.p. 205°–208° C.

A mixture of 1.0 g. of dimethyl N-2-(3-bromodibenzothienyl)fumarate-5-oxide and 10 ml. of diphenyl ether is heated at about 240° C. for about five minutes, then cooled. The product is separated by filtration to provide methyl 5-bromo-1-hydroxy[1]benzothieno[3,2-f]quinoline-3-carboxylate-7-oxide. The product ester is hydrolyzed using the method of Example 32 (or 33) to provide 5-bromo-1-hydroxy[1]benzothieno-[3,2-f]quinoline-3-carboxylic acid-7-oxide, m.p. 289°–290° C. Analysis: Calculated for $C_{16}H_8BrNO_4S$: %C, 49.2; %H, 2.1; %N, 3.6; Found: %C, 48.9; %H, 2.1; %N, 3.6.

EXAMPLE 64

To a solution of 0.6 g. of methyl 5-bromo-1-hydroxy[1]benzothieno[3,2-f]quinoline-3-carboxylate-7-oxide in glacial acetic acid is added excess 30 percent hydrogen peroxide. The mixture is heated to its reflux temperature and maintained at reflux for one hour, then allowed to cool. The precipitate is separated by filtration to give methyl 5-bromo-1-hydroxy[1]-benzothieno[3,2-f]quinoline-3-carboxylate-7,7-dioxide, crude m.p. 240°–260° C. Infrared spectral analysis is consistent with the assigned structure. This ester is hydrolyzed using the method of Example 32 (or 33) to provide 5-bromo-1-hydroxy[1]-benzothieno[3,2-f]quinoline-3-carboxylic acid-7,7-dioxide, m.p. 283°–285° C. (dec.). Analysis: Calculated for $C_{16}H_8BrNO_4S \cdot 3/4H_2O$: %C, 45.8; %H, 2.3; %N, 3.4; Found: %C, 46.1; %H, 2.2; %N, 3.4.

EXAMPLE 65

To a solution of 100 ml. of water and 2 ml. of 10 percent sodium hydroxide solution is added 0.50 g. (1.75 mmoles) of 1-hydroxy[1]benzothieno[3,2-f]quinoline-3-carboxylic acid. To this mixture is added with stirring 50 ml. of N,N-dimethyl formamide and 2.0 g. (6.2 mmoles) of sodium metaperiodate. The mixture is stirred for three days, then filtered. The filtrate is diluted with water and acidified with hydrochloric acid. The resulting product is separated by filtration and washed with water, then dried to provide 1-hydroxy[1-]benzothieno[3,2,-f]quinoline-3-carboxylic acid-7-oxide, m.p. 299°–301° C. Analysis: Calculated for $C_{16}H_9NO_4S \cdot 2/3H_2O$: %C, 59.5; %H, 3.2; %N, 4.3; Found: %C, 59.5; %H, 3.0; %N, 4.4.

What is claimed is:

1. A compound of the formula

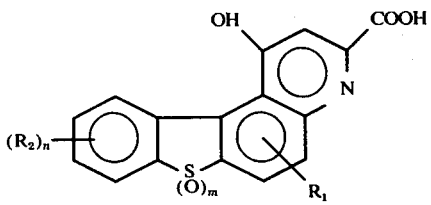

wherein $R_1$ is hydrogen, halogen, lower alkyl or lower alkoxy, $R_2$ is halogen, lower alkyl or lower alkoxy and when n is 2, $R_2$ can represent lower alkyl and lower alkoxy, $m$ is zero, one or two and $n$ is zero, one or two, lower alkyl esters and pharmaceutically acceptable salts thereof.

2. A compound according to claim 1 wherein $R_1$ is hydrogen or halogen.

3. A compound according to claim 1 wherein $m$ is zero or two.

4. A compound according to claim 2 wherein $m$ is zero or two.

5. A compound according to claim 1 wherein $n$ is zero.

6. A compound according to claim 1 wherein n is two.

7. A compound according to claim 2 wherein $n$ is zero or two.

8. A compound according to claim 3 wherein $n$ is zero or two.

9. 1-Hydroxy[1]benzothieno[3,2-f]quinoline-3-carboxylic acid-7,7-dioxide according to claim 1.

10. 1-Hydroxy-10-methyl[1]benzothieno[3,2-f]quinoline-3-carboxylic acid-7-oxide according to claim 1.

11. 1-Hydroxy-10-methyl[1]benzothieno[3,2-f]quinoline-3-carboxylic acid-7,7-dioxide according to claim 1.

12. 1-Hydroxy-10-methoxy[1]benzothieno[3,2-f]quinoline-3-carboxylic acid-7,7-dioxide according to claim 1.

13. 6-Chloro-1-hydroxy[1]benzothieno[3,2-f]quinoline-3-carboxylic acid-7,7-dioxide according to claim 1.

14. 8-Chloro-1-hydroxy[1]benzothieno[3,2-f]quinoline-3-carboxylic acid-7,7-dioxide according to claim 1.

15. 1-Hydroxy-6-methoxy[1]benzothieno[3,2-f]quinoline-3-carboxylic acid-7,7-dioxide according to claim 1.

16. 1-Hydroxy-8-methyl[1]benzothieno[3,2-f]quinoline-3-carboxylic acid-7,7-dioxide according to claim 1.

17. 1-Hydroxy-5-methoxy[1]benzothieno[3,2-f]quinoline-3-carboxylic acid-7,7-dioxide according to claim 1.

18. 5-Bromo-1-hydroxy[1]benzothieno[3,2-f]quinoline-3-carboxylic acid-7,7-dioxide according to claim 1.

19. 9-Chloro-1-hydroxy[1]benzothieno[3,2-f]quinoline-3-carboxylic acid-7,7-dioxide according to claim 1.

20. 5-Bromo-1-hydroxy[1]benzothieno[3,2-f]quinoline-3-carboxylic acid-7-oxide according to claim 1.

21. A compound of the formula

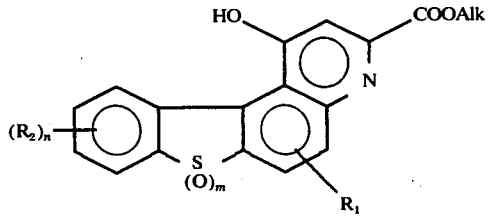

wherein $R_1$ is hydrogen, halogen, lower alkyl or lower alkoxy, $R_2$ is halogen, lower alkyl and/or lower alkoxy, $m$ is zero, one or two, $n$ is zero, one or two and Alk is lower alkyl.

* * * * *

UNITED STATES PATENT AND TRADEMARK OFFICE
CERTIFICATE OF CORRECTION

PATENT NO. : 4,018,780
DATED : April 19, 1977
INVENTOR(S) : LARRY R. LAPPI AND EDWARD H. ERICKSON It is certified that error appears in the above-identified patent and that said Letters Patent are hereby corrected as shown below:

Col. 9, Table I, Example 6, change " 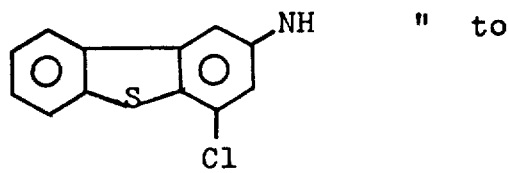 " to
-- 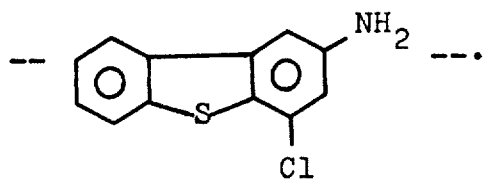 --.

Col. 18, Table II, Example 45, change "389-291(dec)" to
-- 289-291(dec) --.

Signed and Sealed this

*First* Day of *November 1977*

[SEAL]

Attest:

RUTH C. MASON
*Attesting Officer*

LUTRELLE F. PARKER
*Acting Commissioner of Patents and Trademarks*